(12) United States Patent
Medvedev et al.

(10) Patent No.: US 10,980,928 B2
(45) Date of Patent: *Apr. 20, 2021

(54) CARDIAC PUMP WITH SPEED ADAPTED FOR VENTRICLE UNLOADING

(71) Applicant: TC1 LLC, Pleasanton, CA (US)

(72) Inventors: Alexander Medvedev, Ann Arbor, MI (US); Masamichi Yanai, Ann Arbor, MI (US)

(73) Assignee: TC1 LLC, Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/577,242

(22) Filed: Sep. 20, 2019

(65) Prior Publication Data

US 2020/0009307 A1 Jan. 9, 2020

Related U.S. Application Data

(63) Continuation of application No. 15/640,001, filed on Jun. 30, 2017, now Pat. No. 10,456,513, which is a
(Continued)

(51) Int. Cl.
*A61M 1/10* (2006.01)
*A61M 1/12* (2006.01)

(52) U.S. Cl.
CPC .......... *A61M 1/1086* (2013.01); *A61M 1/101* (2013.01); *A61M 1/1005* (2014.02); *A61M 1/122* (2014.02); *A61M 2205/3334* (2013.01)

(58) Field of Classification Search
CPC .. A61M 1/1086; A61M 1/101; A61M 1/1005; A61M 1/122; A61M 2205/3334
See application file for complete search history.

(56) References Cited

U.S. PATENT DOCUMENTS 1,093,868 A 4/1914 Leighty
2,684,035 A 7/1954 Kemp
(Continued)

FOREIGN PATENT DOCUMENTS

CN 102239334 A 11/2011
CN 102341600 A 2/2012
(Continued)

OTHER PUBLICATIONS

Asama, et al., "Suspension Performance of a Two-Axis Actively Regulated Consequent-Pole Bearingless Motor," IEEE Transactions on Energy Conversion, vol. 28, No. 4, Dec. 2013, all pages.
(Continued)

*Primary Examiner* — Mark Bockelman
(74) *Attorney, Agent, or Firm* — Kilpatrick Townsend & Stockton LLP

(57) ABSTRACT

A blood pump system is implantable in a patient for ventricular support. A pumping chamber has an inlet for receiving blood from a ventricle of the patient. An impeller is received in the pumping chamber. A motor is coupled to the impeller for driving rotation of the impeller. A motor controller is provided for tracking systolic and diastolic phases of a cardiac cycle of the patient and supplying a variable voltage signal to the motor in a variable speed mode to produce a variable impeller speed linked to the cardiac cycle. The impeller speed comprises a ramping up to an elevated speed during the diastolic phase in order to reduce a load on the ventricle at the beginning of the systolic phase.

20 Claims, 4 Drawing Sheets

Related U.S. Application Data continuation of application No. 13/873,551, filed on Apr. 30, 2013, now Pat. No. 9,713,663.

(56) References Cited

U.S. PATENT DOCUMENTS

| | | |
|---|---|---|
| 3,510,229 A | 5/1970 | Smith |
| 3,932,069 A | 1/1976 | Giardini et al. |
| 3,960,468 A | 6/1976 | Boorse et al. |
| 4,149,535 A | 4/1979 | Voider |
| 4,382,199 A | 5/1983 | Isaacson |
| 4,392,836 A | 6/1983 | Sugawara |
| 4,507,048 A | 3/1985 | Belenger et al. |
| 4,540,402 A | 9/1985 | Aigner |
| 4,549,860 A | 10/1985 | Yakich |
| 4,686,982 A | 8/1987 | Nash |
| 4,688,998 A | 8/1987 | Olsen et al. |
| 4,753,221 A | 6/1988 | Kensey et al. |
| 4,769,006 A | 9/1988 | Papatonakos |
| 4,790,843 A | 12/1988 | Carpentier et al. |
| 4,806,080 A | 2/1989 | Mizobuchi et al. |
| 4,817,586 A | 4/1989 | Wampler |
| 4,846,152 A | 7/1989 | Wampler et al. |
| 4,888,011 A | 12/1989 | Kung et al. |
| 4,895,557 A | 1/1990 | Moise et al. |
| 4,900,227 A | 2/1990 | Troup Iin |
| 4,902,272 A | 2/1990 | Milder et al. |
| 4,906,229 A | 3/1990 | Wampler |
| 4,908,012 A | 3/1990 | Moise et al. |
| 4,919,647 A | 4/1990 | Nash |
| 4,930,997 A | 6/1990 | Bennett |
| 4,944,722 A | 7/1990 | Carriker et al. |
| 4,957,504 A | 9/1990 | Chardack |
| 4,969,865 A | 11/1990 | Hwang et al. |
| 4,985,014 A | 1/1991 | Orejola |
| 4,995,857 A | 2/1991 | Arnold |
| 5,092,844 A | 3/1992 | Schwartz et al. |
| 5,092,879 A | 3/1992 | Jarvik |
| 5,106,263 A | 4/1992 | Irie |
| 5,106,273 A | 4/1992 | Lemarquand et al. |
| 5,106,372 A | 4/1992 | Ranford |
| 5,112,202 A | 5/1992 | Ozaki et al. |
| 5,129,883 A | 7/1992 | Black |
| 5,145,333 A | 9/1992 | Smith |
| 5,147,186 A | 9/1992 | Buckholtz |
| 5,112,349 A | 12/1992 | Summers et al. |
| 5,190,528 A | 2/1993 | Fonger et al. |
| 5,201,679 A | 4/1993 | Velte et al. |
| 5,211,546 A | 5/1993 | Isaacson et al. |
| 5,275,580 A | 1/1994 | Yamazaki |
| 5,290,227 A | 1/1994 | Pasque |
| 5,360,445 A | 1/1994 | Goldowsky |
| 5,290,236 A | 3/1994 | Mathewson |
| 5,306,295 A | 4/1994 | Kolff et al. |
| 5,312,341 A | 5/1994 | Turi |
| 5,332,374 A | 7/1994 | Kricker et al. |
| 5,346,458 A | 9/1994 | Afield |
| 5,350,283 A | 9/1994 | Nakazeki et al. |
| 5,354,331 A | 11/1994 | Schachar |
| 5,370,509 A | 12/1994 | Golding et al. |
| 5,385,581 A | 1/1995 | Bramm et al. |
| 5,405,383 A | 11/1995 | Barr |
| 5,449,342 A | 12/1995 | Hirose et al. |
| 5,478,222 A | 12/1995 | Heidelberg et al. |
| 5,504,978 A | 4/1996 | Meyer, III |
| 5,507,629 A | 4/1996 | Jarvik |
| 5,533,957 A | 9/1996 | Aldea |
| 5,569,111 A | 10/1996 | Cho et al. |
| 5,575,630 A | 11/1996 | Nakazawa et al. |
| 5,595,762 A | 1/1997 | Derrieu et al. |
| 5,643,226 A | 1/1997 | Cosgrove et al. |
| 5,611,679 A | 3/1997 | Ghosh et al. |
| 5,613,935 A | 3/1997 | Jarvik |
| 5,678,306 A | 10/1997 | Bozeman, Jr. et al. |
| 5,692,882 A | 12/1997 | Bozeman, Jr. et al. |
| 5,695,471 A | 12/1997 | Wampler |
| 5,725,357 A | 3/1998 | Nakazeki et al. |
| 5,738,649 A | 4/1998 | Macoviak |
| 5,746,575 A | 5/1998 | Westphal et al. |
| 5,746,709 A | 5/1998 | Rom et al. |
| 5,755,784 A | 5/1998 | Jarvik |
| 5,776,111 A | 7/1998 | Tesio |
| 5,795,074 A | 8/1998 | Rahman et al. |
| 5,800,559 A | 9/1998 | Higham et al. |
| 5,807,311 A | 9/1998 | Palestrant |
| 5,814,011 A | 9/1998 | Corace |
| 5,824,069 A | 10/1998 | Lemole |
| 5,749,855 A | 12/1998 | Reitan |
| 5,851,174 A | 12/1998 | Jarvik et al. |
| 5,853,394 A | 12/1998 | Tolkoff et al. |
| 5,890,883 A | 4/1999 | Golding et al. |
| 5,924,848 A | 7/1999 | Izraelev |
| 5,924,975 A | 7/1999 | Goldowsky |
| 5,928,131 A | 7/1999 | Prem |
| 5,938,412 A | 8/1999 | Israelev |
| 5,941,813 A | 8/1999 | Sievers et al. |
| 5,868,702 A | 9/1999 | Stevens et al. |
| 5,868,703 A | 9/1999 | Bertolero et al. |
| 5,947,703 A | 9/1999 | Nojiri et al. |
| 5,951,263 A | 9/1999 | Taylor et al. |
| 5,964,694 A | 12/1999 | Siess et al. |
| 6,004,269 A | 12/1999 | Crowley et al. |
| 6,007,479 A | 12/1999 | Rottenberg et al. |
| 6,030,188 A | 2/2000 | Nojiri et al. |
| 6,042,347 A | 3/2000 | Scholl et al. |
| 6,053,705 A | 4/2000 | Schob et al. |
| 6,066,086 A | 5/2000 | Antaki et al. |
| 6,071,093 A | 6/2000 | Hart |
| 6,074,180 A | 6/2000 | Khanwilkar et al. |
| 6,080,133 A | 6/2000 | Wampler |
| 6,082,900 A | 7/2000 | Takeuchi et al. |
| 6,100,618 A | 8/2000 | Schoeb et al. |
| 6,058,593 A | 9/2000 | Siess |
| 6,123,659 A | 9/2000 | leBlanc et al. |
| 6,123,726 A | 9/2000 | Mori et al. |
| 6,139,487 A | 10/2000 | Siess |
| 6,086,527 A | 11/2000 | Talpade |
| 6,142,752 A | 11/2000 | Akamatsu et al. |
| 6,143,025 A | 11/2000 | Stobie et al. |
| 6,146,325 A | 11/2000 | Lewis et al. |
| 6,149,683 A | 11/2000 | Lancisi et al. |
| 6,158,984 A | 12/2000 | Cao et al. |
| 6,171,078 B1 | 1/2001 | Schob |
| 6,176,822 B1 | 1/2001 | Nix et al. |
| 6,176,848 B1 | 1/2001 | Rau et al. |
| 6,190,304 B1 | 2/2001 | Downey et al. |
| 6,206,659 B1 | 3/2001 | Izraelev |
| 6,254,359 B1 | 3/2001 | Aber |
| 6,227,797 B1 | 5/2001 | Watterson et al. |
| 6,227,820 B1 | 5/2001 | Jarvik |
| 6,234,772 B1 | 5/2001 | Wampler et al. |
| 6,234,998 B1 | 5/2001 | Wampler |
| 6,247,892 B1 | 6/2001 | Kazatchkov et al. |
| 6,264,635 B1 | 7/2001 | Wampler et al. |
| 6,293,901 B1 | 9/2001 | Prem |
| 6,295,877 B1 | 10/2001 | Aboul-Hosn et al. |
| 6,319,231 B1 | 11/2001 | Andrulitis |
| 6,245,007 B1 | 12/2001 | Bedingham et al. |
| 6,458,163 B1 | 1/2002 | Slemker et al. |
| 6,351,048 B1 | 2/2002 | Schob et al. |
| 6,375,607 B1 | 4/2002 | Prem |
| 6,422,990 B1 | 7/2002 | Prem |
| 6,425,007 B1 | 7/2002 | Messinger |
| 6,428,464 B1 | 8/2002 | Bolling |
| 6,439,845 B1 | 8/2002 | Veres |
| 6,447,266 B2 | 9/2002 | Antaki et al. |
| 6,447,441 B1 | 9/2002 | Yu et al. |
| 6,508,777 B1 | 1/2003 | Macoviak et al. |
| 6,508,787 B2 | 1/2003 | Erbel et al. |
| 6,532,964 B2 | 3/2003 | Aboul-Hosn et al. |
| 6,533,716 B1 | 3/2003 | Schmitz-Rode et al. |
| 6,544,216 B1 | 4/2003 | Sammler et al. |
| 6,547,519 B2 | 4/2003 | deBlanc et al. |
| 6,547,530 B2 | 4/2003 | Ozaki et al. |
| 6,595,762 B2 | 7/2003 | Khanwilkar et al. |

(56) References Cited

U.S. PATENT DOCUMENTS

| | | |
|---|---|---|
| 6,609,883 B2 | 8/2003 | Woodard et al. |
| 6,623,420 B2 | 9/2003 | Reich et al. |
| 6,641,558 B1 | 11/2003 | Aboul-Hosn et al. |
| 6,688,861 B2 | 2/2004 | Wampler |
| 6,692,318 B2 | 2/2004 | McBride |
| 6,698,097 B1 | 3/2004 | Miura et al. |
| 6,709,418 B1 | 3/2004 | Aboul-Hosn et al. |
| 6,716,189 B1 | 4/2004 | Jarvik et al. |
| 6,776,578 B2 | 8/2004 | Belady |
| 6,790,171 B1 | 9/2004 | Griindeman et al. |
| 6,794,789 B2 | 9/2004 | Siess et al. |
| 6,808,371 B2 | 10/2004 | Niwatsukino et al. |
| 6,817,836 B2 | 11/2004 | Nose et al. |
| 6,860,713 B2 | 1/2005 | Hoover |
| 6,935,344 B1 | 8/2005 | Aboul-Hosn et al. |
| 6,926,662 B1 | 9/2005 | Aboul-Hosn et al. |
| 6,942,672 B2 | 9/2005 | Heilman et al. |
| 6,949,066 B2 | 9/2005 | Beamson et al. |
| 6,974,436 B1 | 12/2005 | Aboul-Hosn et al. |
| 6,991,595 B2 | 1/2006 | Burke et al. |
| 7,010,954 B2 | 3/2006 | Siess et al. |
| 7,011,620 B1 | 3/2006 | Siess |
| 7,048,681 B2 | 5/2006 | Tsubouchi et al. |
| 7,112,903 B1 | 9/2006 | Schob |
| 7,128,538 B2 | 10/2006 | Tsubouchi et al. |
| 7,027,875 B2 | 11/2006 | Siess et al. |
| 7,156,802 B2 | 1/2007 | Woodard et al. |
| 7,160,243 B2 | 1/2007 | Medvedev |
| 7,175,588 B2 | 2/2007 | Morello |
| 7,172,551 B2 | 6/2007 | Leasure |
| 7,241,257 B1 | 10/2007 | Ainsworth et al. |
| 7,331,921 B2 | 2/2008 | Viole et al. |
| 7,335,192 B2 | 2/2008 | Keren et al. |
| 7,431,688 B2 | 10/2008 | Wampler et al. |
| 7,329,236 B2 | 12/2008 | Kesten et al. |
| 7,467,930 B2 | 12/2008 | Ozaki et al. |
| 7,470,246 B2 | 12/2008 | Mori et al. |
| 7,491,163 B2 | 2/2009 | Viole et al. |
| 7,575,423 B2 | 8/2009 | Wampler |
| 7,645,225 B2 | 1/2010 | Medvedev et al. |
| 7,699,586 B2 | 4/2010 | LaRose et al. |
| 7,748,964 B2 | 7/2010 | Yaegashi et al. |
| 7,731,675 B2 | 8/2010 | Aboul-Hosn et al. |
| 7,802,966 B2 | 9/2010 | Wampler et al. |
| 7,841,976 B2 | 11/2010 | McBride et al. |
| 7,888,242 B2 | 2/2011 | Tanaka et al. |
| 7,934,909 B2 | 5/2011 | Nuesser et al. |
| 7,976,271 B2 | 7/2011 | LaRose et al. |
| 7,997,854 B2 | 8/2011 | LaRose et al. |
| 8,007,254 B2 | 8/2011 | LaRose et al. |
| 8,096,935 B2 | 1/2012 | Sutton et al. |
| 8,123,669 B2 | 2/2012 | Siess et al. |
| 8,226,373 B2 | 7/2012 | Yaehashi |
| 8,282,359 B2 | 10/2012 | Ayre et al. |
| 8,283,829 B2 | 10/2012 | Yamamoto et al. |
| 8,366,381 B2 | 2/2013 | Woodard et al. |
| 8,403,823 B2 | 3/2013 | Yu et al. |
| 8,512,012 B2 | 8/2013 | Mustafa et al. |
| 8,652,024 B1 | 2/2014 | Yanai et al. |
| 9,713,663 B2 | 7/2017 | Medvedev et al. |
| 10,456,513 B2 | 10/2019 | Medvedev et al. |
| 2002/0058994 A1 | 5/2002 | Hill et al. |
| 2002/0095210 A1 | 7/2002 | Finnegan et al. |
| 2003/0023302 A1 | 1/2003 | Moe et al. |
| 2003/0045772 A1 | 3/2003 | Reich et al. |
| 2003/0199727 A1 | 10/2003 | Burke et al. |
| 2004/0007515 A1 | 1/2004 | Geyer |
| 2004/0024285 A1 | 2/2004 | Muckter |
| 2004/0030381 A1 | 2/2004 | Shu |
| 2004/0210305 A1 | 10/2004 | Shu et al. |
| 2005/0089422 A1 | 4/2005 | Ozaki et al. |
| 2005/0131271 A1 | 6/2005 | Benkowski et al. |
| 2005/0287022 A1 | 12/2005 | Yaehashi et al. |
| 2006/0024182 A1 | 2/2006 | Akdis et al. |
| 2006/0055274 A1 | 3/2006 | Kim |
| 2007/0078293 A1 | 4/2007 | Shambaugh, Jr. |
| 2007/0134993 A1 | 6/2007 | Tamez et al. |
| 2007/0208210 A1 | 9/2007 | Gelfand et al. |
| 2007/0213690 A1 | 9/2007 | Phillips et al. |
| 2007/0231135 A1 | 10/2007 | Wampler et al. |
| 2007/0297923 A1 | 12/2007 | Tada |
| 2008/0021394 A1 | 1/2008 | La Rose et al. |
| 2008/0030895 A1 | 2/2008 | Obara et al. |
| 2008/0124231 A1 | 5/2008 | Yaegashi |
| 2009/0060743 A1 | 3/2009 | McBride et al. |
| 2009/0074336 A1 | 3/2009 | Engesser et al. |
| 2009/0171136 A1 | 7/2009 | Shambaugh, Jr. |
| 2010/0222634 A1 | 9/2010 | Poirier |
| 2010/0256440 A1 | 10/2010 | Maher et al. |
| 2011/0112354 A1 | 5/2011 | Nishimura et al. |
| 2011/0118766 A1 | 5/2011 | Reichenbach et al. |
| 2011/0118829 A1 | 5/2011 | Hoarau et al. |
| 2011/0129373 A1 | 6/2011 | Mori |
| 2011/0243759 A1 | 10/2011 | Ozaki et al. |
| 2011/0298304 A1 | 12/2011 | Cotter |
| 2011/0318203 A1 | 12/2011 | Ozaki et al. |
| 2012/0003108 A1 | 1/2012 | Ozaki et al. |
| 2012/0016178 A1 | 1/2012 | Woodard et al. |
| 2012/0022645 A1 | 1/2012 | Burke |
| 2012/0035411 A1 | 2/2012 | LaRose et al. |
| 2012/0078030 A1 | 3/2012 | Bourque |
| 2012/0130152 A1 | 5/2012 | Ozaki et al. |
| 2012/0243759 A1 | 9/2012 | Fujisawa |
| 2012/0308363 A1 | 12/2012 | Ozaki et al. |
| 2013/0121821 A1 | 5/2013 | Ozaki et al. |
| 2013/0170970 A1 | 7/2013 | Ozaki et al. |
| 2013/0178694 A1 | 7/2013 | Jeffery et al. |
| 2013/0243623 A1 | 9/2013 | Okawa et al. |
| 2014/0030122 A1 | 1/2014 | Ozaki et al. |
| 2014/0323796 A1 | 10/2014 | Medvedev et al. |
| 2015/0017030 A1 | 1/2015 | Ozaki |

FOREIGN PATENT DOCUMENTS

| | | |
|---|---|---|
| EP | 1113117 A2 | 7/2001 |
| EP | 1495773 A2 | 1/2005 |
| EP | 2298375 A1 | 3/2011 |
| EP | 2372160 A1 | 10/2011 |
| EP | 2405140 A1 | 1/2012 |
| EP | 2461465 A1 | 6/2012 |
| EP | 3013385 A2 | 5/2016 |
| JP | 58-009535 | 1/1983 |
| JP | 61-293146 | 12/1986 |
| JP | 04-091396 A | 3/1992 |
| JP | H04-148094 A | 5/1992 |
| JP | 05-021197 U | 3/1993 |
| JP | H06-014538 U | 2/1994 |
| JP | 06-053790 U | 7/1994 |
| JP | 2006-070476 U | 9/1994 |
| JP | 2006-245455 | 9/1994 |
| JP | 07-014220 U | 3/1995 |
| JP | H07-042869 U | 8/1995 |
| JP | H07-509156 A | 10/1995 |
| JP | 09-122228 A | 5/1997 |
| JP | H10-331841 A | 12/1998 |
| JP | 11-244377 A | 9/1999 |
| JP | 2001-309628 A | 11/2001 |
| JP | 2003-135592 A | 5/2003 |
| JP | 2004-166401 A | 6/2004 |
| JP | 2004-209240 A | 7/2004 |
| JP | 2004-332566 A | 11/2004 |
| JP | 2004-346925 A | 12/2004 |
| JP | 2005-94955 | 4/2005 |
| JP | 2005-127222 A | 5/2005 |
| JP | 2005-245138 | 9/2005 |
| JP | 2005-270345 A | 10/2005 |
| JP | 2005-270415 A | 10/2005 |
| JP | 2005-287599 A | 10/2005 |
| JP | 2006-167173 A | 6/2006 |
| JP | 2007-002885 A | 1/2007 |
| JP | 2007-043821 A | 2/2007 |
| JP | 2007-089972 A | 4/2007 |
| JP | 2007-089974 A | 4/2007 |
| JP | 2007-215292 A | 8/2007 |

(56) References Cited

FOREIGN PATENT DOCUMENTS

| | | |
|---|---|---|
| JP | 2007-247489 A | 9/2007 |
| JP | 2008-011611 | 1/2008 |
| JP | 2008-104278 A | 5/2008 |
| JP | 2008-132131 A | 6/2008 |
| JP | 2008-099453 | 8/2008 |
| JP | 2008-193838 | 8/2008 |
| JP | 2008-297997 A | 12/2008 |
| JP | 2008-301634 | 12/2008 |
| JP | 2006-254619 | 9/2009 |
| JP | 2010-136863 A | 6/2010 |
| JP | 2012-021413 A | 2/2012 |
| WO | 1993-07388 A1 | 4/1993 |
| WO | 1996-31934 A1 | 10/1996 |
| WO | 1997-42413 A1 | 11/1997 |
| WO | 2005-028000 A1 | 3/2005 |
| WO | 2005-034312 A2 | 4/2005 |
| WO | 2009-150893 A1 | 12/2009 |
| WO | 2009-157408 A1 | 12/2009 |
| WO | 2010-067682 A1 | 6/2010 |
| WO | 2010-101082 A1 | 9/2010 |
| WO | 2011-013483 A1 | 2/2011 |
| WO | 2011-090927 A1 | 7/2011 |
| WO | 2012-047550 A1 | 4/2012 |
| WO | 2014-116639 A1 | 7/2014 |
| WO | 2014-179271 A2 | 11/2014 |

OTHER PUBLICATIONS

Terumo Heart, Inc., "Handled With Care—Significantly Reduce the Risk of Cell Damage," Terumo brochure, Apr. 2010, all pages.
Yamazaki, et al., "Development of a Miniature Intraventricular Axial Flow Blood Pump," ASAIO Journal, 1993, all pages.
Kosaka, et al.; "Operating Point Control System for a Continuous Flow Artificial Heart: In Vitro Study"; ASAIO Journal 2003, all pages.
Extended European Search report dated Apr. 2, 2013 in European Patent Application No. 10748702.7, all pages.
Extended European Search report dated Nov. 19, 2012 in European Patent Application No. 10748677.1, all pages.
International Search Report and Written Opinion dated Jul. 14, 2009 in International Patent Application No. PCT/JP2009/061318, filed Jun. 22, 2009, all pages.
International Preliminary Report on Patentability dated Feb. 8, 2011 in International Patent Application No. PCT/JP2009/061318, filed Jun. 22, 2009, all pages.
International Search Report and Written Opinion dated Apr. 12, 2011 in International Patent Application No. PCT/JP2011/050925, filed Feb. 24, 2011, all pages.
International Preliminary Report on Patentability dated Sep. 18, 2012 in International Patent Application No. PCT/JP2011/050925, filed Jan. 20, 2011, all pages.
International Search Report and Written Opinion dated Apr. 12, 2011 in International Patent Application No. PCT/JP2011/054134, filed Jun. 22, 2009, all pages.
International Preliminary Report on Patentability dated Oct. 23, 2012 in International Patent Application No. PCT/JP2011/054134, filed Jun. 22, 2009, all pages.
International Search Report and Written Opinion dated Sep. 13, 2011 in International Patent Application No. PCT/JP2011/064768, filed Jun. 28, 2011 all pages.
International Preliminary Report on Patentability dated Feb. 12, 2013 in International Patent Application No. PCT/JP2011/064768, filed Jun. 28, 2011 all pages.
Extended European Search report dated Jan. 1, 2013 in European Patent Application No. 09831788.6, all pages.
Decision to Grant dated Aug. 27, 2020 in European Patent Application No. 14792355.1, 2 pages.

CARDIAC PUMP WITH SPEED ADAPTED FOR VENTRICLE UNLOADING

CROSS REFERENCE TO RELATED APPLICATIONS

This application is a continuation of U.S. application Ser. No. 15/640,001, filed on Jun. 30, 2017, which is a continuation of U.S. application Ser. No. 13/873,551, filed on Apr. 30, 2013, now U.S. Pat. No. 9,713,663, the disclosures of which are incorporated herein by reference in its entirety, for all purposes, as if fully set forth herein.

STATEMENT REGARDING FEDERALLY SPONSORED RESEARCH

Not Applicable.

BACKGROUND OF THE INVENTION

The present invention relates in general to ventricular support pumps and controls, and, more specifically, to a ventricular assist device for reducing load applied to a weakened ventricle during the systolic phase.

Many types of circulatory assist devices are available for either short term or long term support for patients having cardiovascular disease. For example, a heart pump system known as a left ventricular assist device (LVAD) can provide long term patient support with an implantable pump associated with an externally-worn pump control unit and batteries. The LVAD improves circulation throughout the body by assisting the left side of the heart in pumping blood. One such system is the DuraHeart® LVAS system made by Terumo Heart. Inc., of Ann Arbor, Mich. The DuraHeart® system employs a centrifugal pump with a magnetically levitated impeller to pump blood from the left ventricle to the aorta. The impeller can act as a rotor of an electric motor in which a rotating magnetic field from a multiphase stator couples with the impeller and is rotated at a speed appropriate to obtain the desired blood flow through the pump.

A typical cardiac assist system includes a pumping unit, drive electronics, microprocessor control unit, and an energy source such as rechargeable batteries and/or an AC power conditioning circuit. The system is implanted during a surgical procedure in which a centrifugal pump is placed in the patient's chest. An inflow conduit is pierced into the left ventricle to supply blood to the pump. One end of an outflow conduit is mechanically fitted to the pump outlet and the other end is surgically attached to the patient's aorta by anastomosis. A percutaneous cable connects to the pump, exits the patient through an incision, and connects to the external control unit. An LVAD system may be used with or without a pacemaker.

A control system for varying pump speed to achieve a target blood flow based on physiologic conditions is shown in U.S. Pat. No. 7,160,243, issued Jan. 9, 2007, which is incorporated herein by reference in its entirety. A target blood flow rate may be established based on the patient's heart rate so that the physiologic demand is met. In one type of conventional control unit, a constant speed setpoint has been determined for the pump motor to achieve the target flow based on demand. In this type of system, the pump speed is substantially constant within an individual cardiac cycle.

Pulsatile pumping systems are also known wherein the pump speed is varied within the cardiac cycle to more closely mimic natural heart action. In one example, U.S. Pat. No. 8,096,935 to Sutton et al oscillates the speed of the pump to produce a pulsed pressure. The speed is oscillated synchronously with the natural cardiac cycle such that a pump speed is increased during systole (the time of highest flow) and decreased during diastole (the time of lowest flow).

Whether operated at a constant speed or in a pulsatile manner, it is known that when desiring to obtain a maximum unloading of a weakened ventricle the average pump speed should be increased as much as possible (so that the pump flow is increased to the point where it captures almost the entire cardiac output). Due to flow inertia, however, the pump flow lags the ventricular pressure increase occurring at the beginning of systole. Therefore, the ventricle contraction still remains isometric at the beginning of systole (i.e., the pressure inside the ventricle resists its contraction). Furthermore, an increased average pump speed increases the risk of ventricular suction, particularly at the end of systole when the ventricle could be nearly empty.

SUMMARY OF THE INVENTION

In order to make ventricular contraction easier, the pump speed is increased before the systolic phase of cardiac cycle. As a result, the intra-ventricular pressure is reduced prior to ventricular contraction allowing a weak ventricle to contract with reduced resistance. In order to prevent ventricular suction, the pump speed is reduced to before the end of systole when the ventricle is nearly empty.

In one aspect of the invention, a blood pump system is provided for implanting in a patient for ventricular support. A pumping chamber has an inlet for receiving blood from a ventricle of the patient. An impeller is received in the pumping chamber. A motor is coupled to the impeller for driving rotation of the impeller. A motor controller is provided for tracking systolic and diastolic phases of a cardiac cycle of the patient and supplying a variable voltage signal to the motor in a variable speed mode to produce a variable impeller speed linked to the cardiac cycle. The impeller speed comprises a ramping up to an elevated speed during the diastolic phase in order to reduce a load on the ventricle at the beginning of the systolic phase. In some embodiments, the impeller speed also comprises a ramping down to a reduced speed during the systolic phase to avoid collapse of the ventricle.

The variable speed mode may be comprised of a constant current mode or may be comprised of a speed control for matching impeller speed to a target speed in which the target speed ramps up to the elevated speed during the diastolic phase and ramps down to a reduced speed during the systolic phase to avoid collapse of the ventricle.

The motor controller may be configurable to provide the variable voltage signal to the motor in either the above variable speed mode or a constant speed mode. The constant speed mode maintains a substantially constant speed of the impeller over each respective cardiac cycle. A selection between the variable speed mode and the constant speed mode is determined according to a physiologic capability of the patient. This allows for selective therapy during LVAD support. For example, immediately following the implantation when the left ventricle is weak, the pump is set to operate in the constant current mode thereby providing a greater level of ventricle unloading. With the patient's recovery, the pump may be set to operate in the constant speed mode, promoting higher flow pulsatility and a more natural physiologic response to the patient's activities.

DETAILED DESCRIPTION OF PREFERRED EMBODIMENTS

Figure 1:
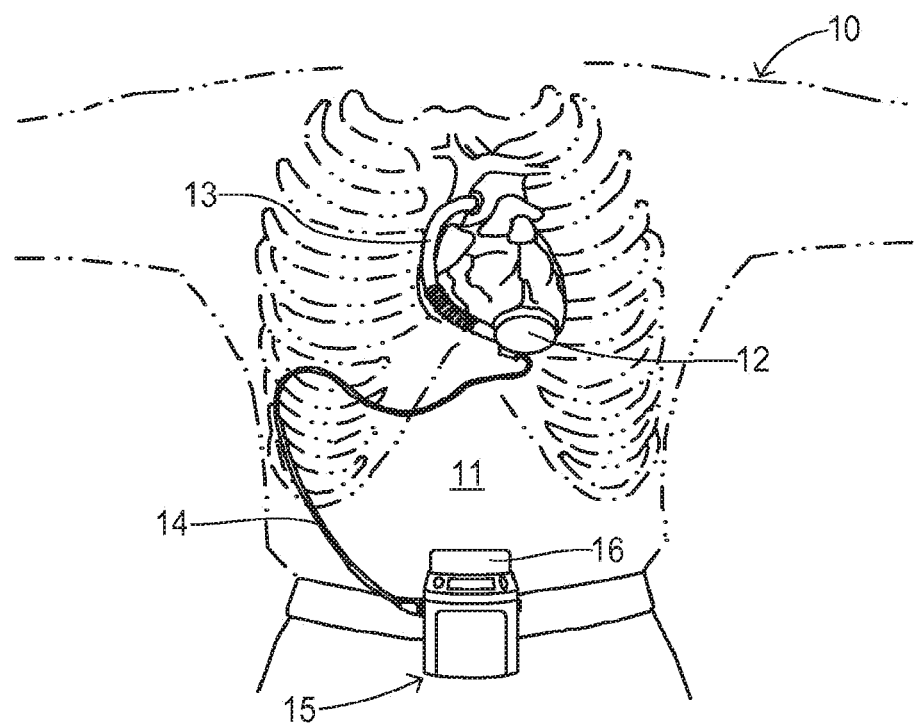
FIG. 1 is a diagram of a circulatory assist system as one example of an implantable pump employing the present invention.

Referring to FIG. 1, a patient 10 is shown in fragmentary front elevational view. Surgically implanted either into the patient's abdominal cavity or pericardium 11 is the pumping unit 12 of a ventricular assist device. An inflow conduit (on the hidden side of unit 12) pierces the heart to convey blood from the patient's left ventricle into pumping unit 12. An outflow conduit 13 conveys blood from pumping unit 12 to the patient's aorta. A percutaneous power cable 14 extends from pumping unit 12 outwardly of the patient's body via an incision to a compact control unit 15 worn by patient 10. Control unit 15 is powered by a main battery pack 16 and/or an external AC power supply and an internal backup battery. Control unit 15 includes a commutator circuit for driving a motor within pumping unit 12.

Figure 2:
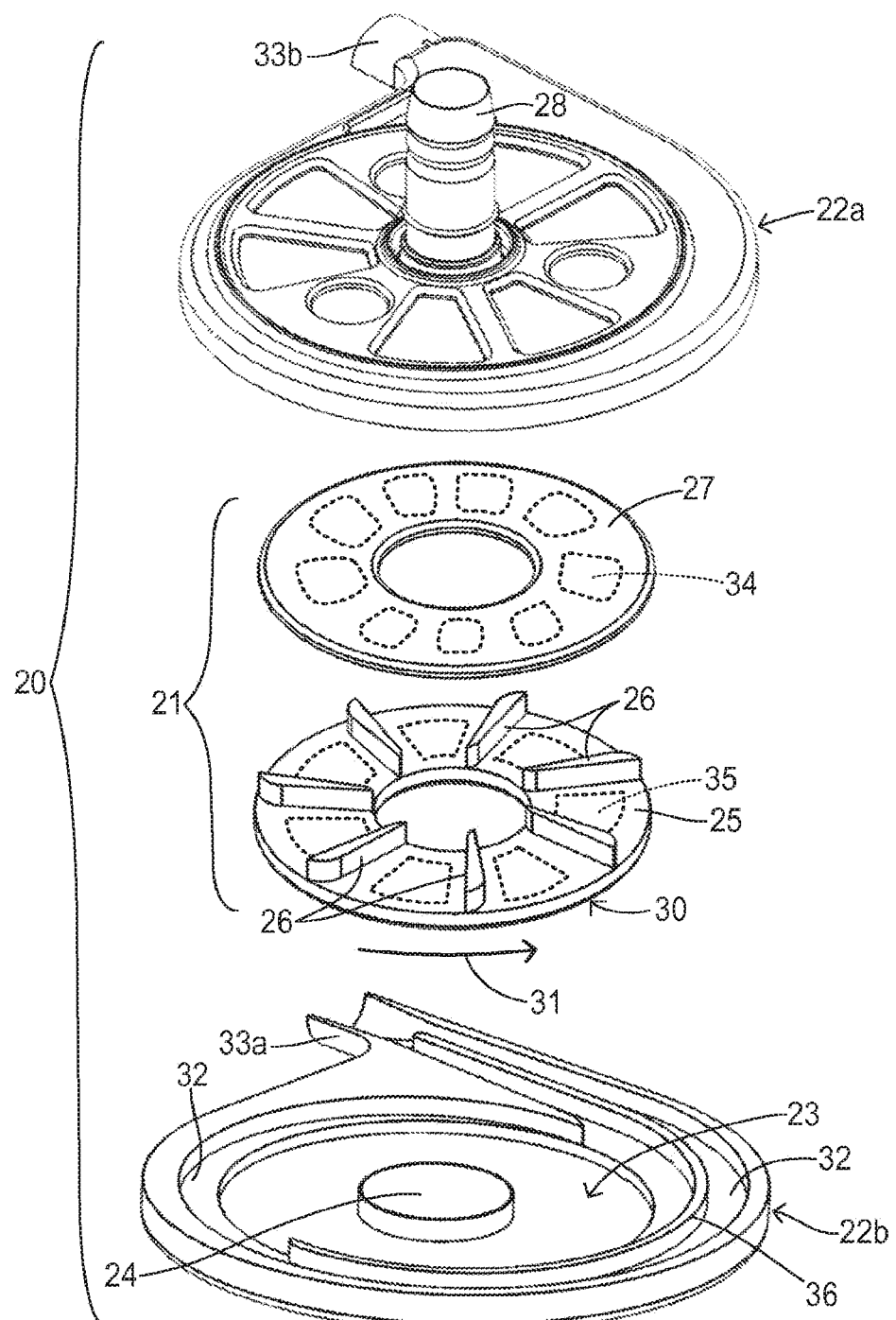
FIG. 2 is an exploded, perspective view of a portion of a centrifugal pump of a type that can be used in the present invention.

FIG. 2 shows a centrifugal pump unit 20 having an impeller 21 and a pump housing having upper and lower halves 22a and 22b. Impeller 21 is disposed within a pumping chamber 23 over a hub 24. Impeller 21 includes a first plate or disc 25 and a second plate or disc 27 sandwiched over a plurality of vanes 26. Second disc 27 includes a plurality of embedded magnet segments 34 for interacting with a levitating magnetic field created by a levitation magnet structure (not shown) that would be disposed against or incorporated in housing 22a. First disc 25 also contains embedded magnet segments 35 for magnetically coupling with a magnetic field from a motor (not shown) disposed against or incorporated in housing 22b. Housing 22a includes an inlet 28 for receiving blood from a patient's ventricle and distributing it to vanes 26. Impeller 21 is preferably circular and has an outer circumferential edge 30. By rotatably driving impeller 21 in a pumping direction 31, the blood received at an inner edge of impeller 21 is carried to outer circumferential 30 and enters a volute region 32 within pumping chamber 23 at an increased pressure. The pressurized blood flows out from an outlet 33 formed by housing features 33a and 33b. A flow-dividing guide wall 36 may be provided within volute region 32 to help stabilize the overall flow and the forces acting on impeller 21.

Figure 3:
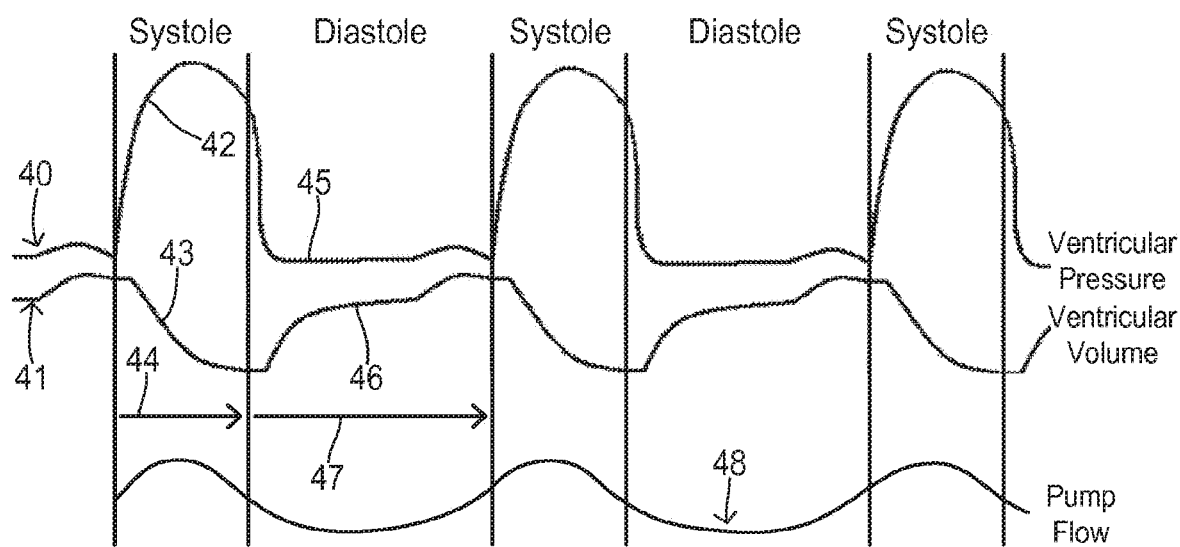
FIG. 3 is a diagram showing a prior art variable speed profile synchronized with a cardiac cycle.

FIG. 3 shows a ventricular pressure curve 40 and a ventricular volume curve 41 according to a typical cardiac cycle. A pressure pulse 42 and a volume ejection 43 correspond with a systolic phase 44. A low ventricular pressure 45 and increasing ventricular volume 46 correspond with a diastolic phase 47. The start of systole corresponds with the time that the mitral or tricuspid valve closes, and the start of diastole corresponds with the time that the aortic valve or pulmonary valve closes. Curve 48 shows a pulsatile pump flow in which the pump speed is synchronously varied in order to provide an increased speed during systolic phase 44 and a decreased speed during diastolic phase 47. As explained above, this conventional pulsatile flow does not significantly unload the ventricle at the beginning of systole.

Figure 4:
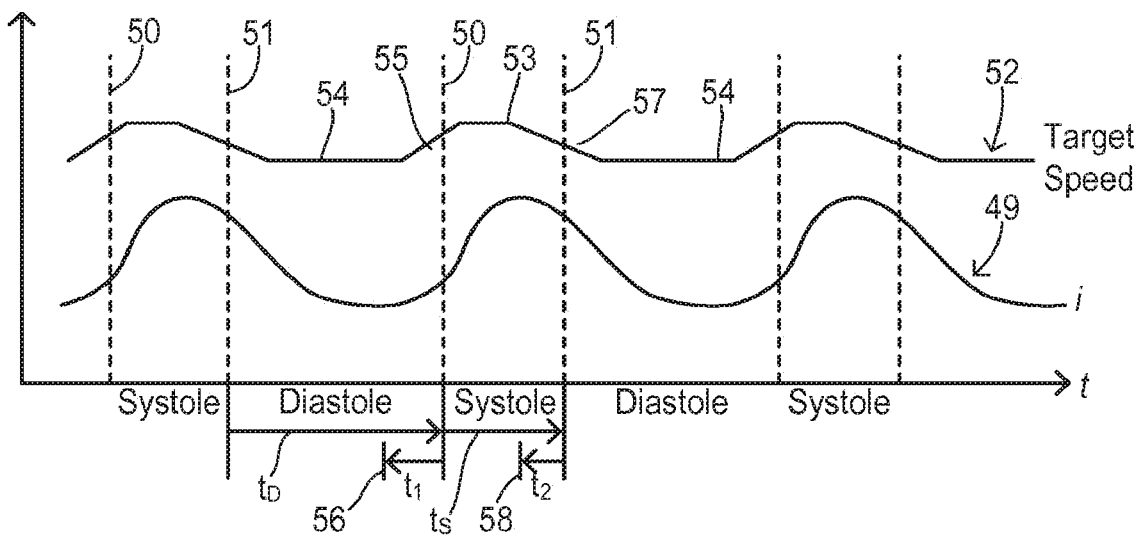
FIG. 4 is a diagram showing a variable speed profile of the present invention.
Figure 5:
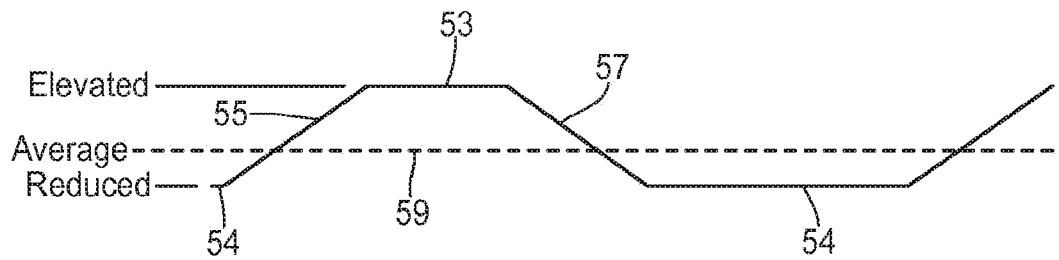
FIG. 5 is a diagram showing a variable speed profile in greater detail.

FIGS. 4 and 5 show a first embodiment of the invention for providing a variable speed mode with certain speed changes preceding the beginning of systole 50 and the beginning of diastole 51. An impeller speed curve 52 provides a pulsatile flow between an elevated speed 53 and a reduced speed 54. Curve 49 shows a representative current vector applied to the motor by the motor controller in order to generate a corresponding target speed. Thus, an increase in current generates a speed increase and a decrease in current generates a speed decrease. The target speed includes a ramping up at segment 55 from reduced speed 54 to elevated speed 53, wherein the ramping up begins during diastole. The time of increase and the slope of the increase are configured to provide an increasing flow before systole begins to provide a reduced ventricular pressure that allows a weak ventricle to contract with reduced resistance. The controlled motor current 49 begins to increase at a time 56 which precedes systole by a time period $t_1$. The beginning of ramping up segment 55 of the speed may lag the current increase but still occurs prior to the beginning of systole 50. Preferably, time 56 is scheduled by the motor controller at time $t_1$ before the next expected occurrence of systole 50 such that the ramping up begins at a moment between about 50% to about 90% into the diastolic phase. Thus, denoting the length of the diastolic phase as $t_D$, the ratio $t_1/t_D$ is preferably between 0.1 and 0.5.

To help avoid collapse of the ventricle toward the end of systole or during diastole, impeller speed 52 preferably ramps down at segment 57 from elevated speed 53 to reduced speed 54. Segment 57 begins during the systolic phase of the cardiac cycle (i.e., before the beginning of diastole 51). For example, current curve 49 starts to ramp down at a time 58 which precedes start of diastole 51 by a time $t_2$. Preferably, time 58 may be at a moment between about 50% to about 90% into the systolic phase. Thus, denoting the length of the systolic phase as $t_s$, the ratio $t_1/t_s$ is preferably between 0.1 and 0.5.

As shown in FIG. 5, an average speed 59 is maintained as the instantaneous speed varies between elevated speed 53 and reduced speed 54. Average speed 59 may be determined in a conventional manner according to the physiological state of the patient. Offsets from average speed 59 for elevated speed 53 and reduced speed 54 may be substantially constant or may also be determined according to the physiological state of the patient.

Figure 6:
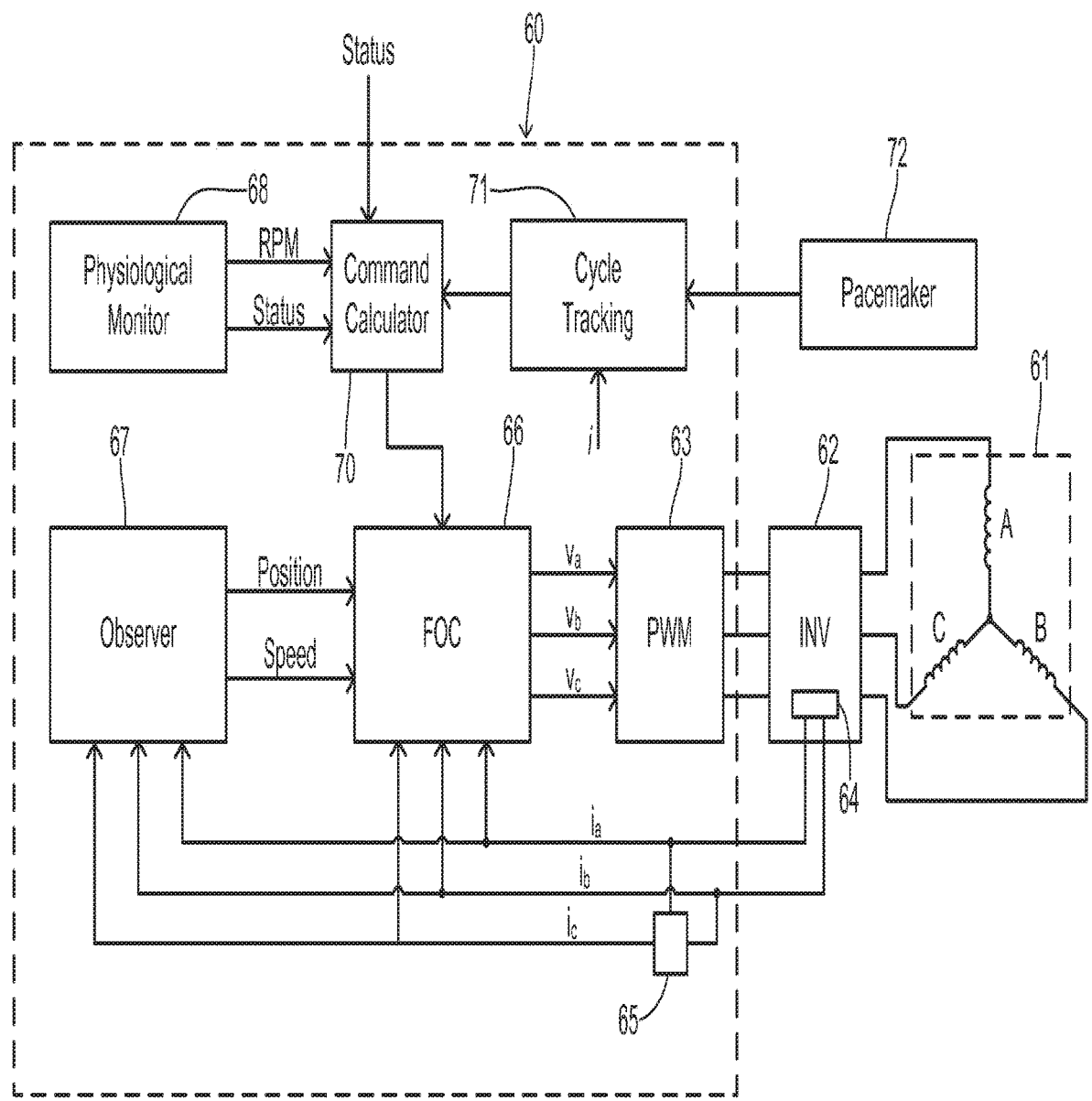
FIG. 6 is a block diagram showing a pump motor and control system of the present invention.

A pump system of the present invention is shown in greater detail in FIG. 6 wherein a controller 60 uses field oriented control (FOC) to supply a multiphase voltage signal to the pump motor which comprises a stator assembly 61 shown as a three-phase stator. Individual phases A, B, and C are driven by an H-bridge inverter 62 functioning as a commutation circuit driven by a pulse width modulator (PWM) circuit 63 in controller 60. A current sensing circuit 64 associated with inverter 62 measures instantaneous phase current in at least two phases providing current signals designated $i_a$ and $i_b$. A current calculating block 65 receives the two measured currents and calculates a current $i_c$ corresponding to the third phase as known in the art. The measured currents are input to an FOC block 66 and to a current observer block 67 which estimates the position and speed of the impeller as known in the art. The impeller position and speed are input to FOC block 66.

An average target speed or rpm for operating the pump is provided by a physiological monitor 68 to FOC block 66. The average rpm may be set by a medical caregiver or may be determined according to an algorithm based on various patient parameters such heart beat. Monitor 68 may also generate a status signal for identifying whether the ventricle is in the initial, highly weakened state or whether a predetermined recovery has been obtained in the strength of the ventricle. The average rpm and the status signal are provided to a speed command calculator 70. The status signal can be used to determine whether or not the variable speed control of the invention should be used to unload the ventricle. The status signal can alternatively be externally provided to calculator 70 (e.g., by a physician via an HMI).

Command calculator 70 is coupled to a cycle tracking block 71 which maintains timing for a cardiac cycle reference. A current signal (e.g., currents $i_a$, $i_b$, and $i_c$) can be used in order to detect the cardiac cycle from the instantaneous blood flow, for example. More specifically, the controller may identify the heart rate by measuring time between current peaks in the speed control mode. Then the speed decrease can start at a calculated time after the occurrence of a current peak. The speed increase can start at a calculated time after the current minimum value is to detected. This calculated time typically depends on the heart rate.

Alternatively, cycle tracking block 71 can be coupled to a pacemaker 72 in the event that the patient is using such a device. Conventional pacemakers have been constructed to continuously generate radio signals that contain information about pulse timing and other data. These sine-wave modulated signals can be received by a special receiver (not shown), where the signals are demodulated, digitized (if necessary), and transferred to cycle tracking block 71. Besides being located near the implanted pacemaker and connected by a cable or wirelessly to the controller (e.g., via BlueTooth), a receiver could be integrated with the controller or the pumping unit.

Based on the reference cycle timing from block 71, command calculator 70 determines an instantaneous speed (or magnitude of the current vector) to be used by FOC block 66. FOC block 66 generates commanded voltage output values $v_a$, $v_b$, and $v_c$ which are input to PWM block 63. The $v_a$, $v_b$, and $v_c$ commands may also be coupled to observer 67 for use in detecting speed and position (not shown). Thus, the speed is controlled to follow the curves shown in FIGS. 4 and 5.

In one embodiment, the timing of the speed increases and decreases are determined as follows. At a constant pacing rate (i.e., constant beat rate), the time for starting the speed acceleration (e.g., at time 56 in FIG. 4) is:

$$t_{acc}(n+1)=t_p(n)+60/N-t_1.$$

where $t_p(n)$ is the time of occurrence of a pacemaker pulse time signaling the start of the current cardiac cycle; N is the heart (pulse) rate in beat/min set by a pacemaker; and $t_{acc}(n+1)$ is the time to increase the pump speed for the next cardiac cycle. Similarly, the time to start deceleration (e.g., at a time 58 in FIG. 4) is:

$$t_{decel}(n+1)=t_a(n+1)+t_s$$

where $t_s$ is the duration of systole. Systole typically lasts 30% to 50% of the cardiac cycle 60/N, and within a certain heart rate range it is fairly independent of the heart rate N. For example, for a heart rate N between 60-120 beats/min, $t_s$ is between 0.30 seconds and 0.25 seconds.

Figure 7:
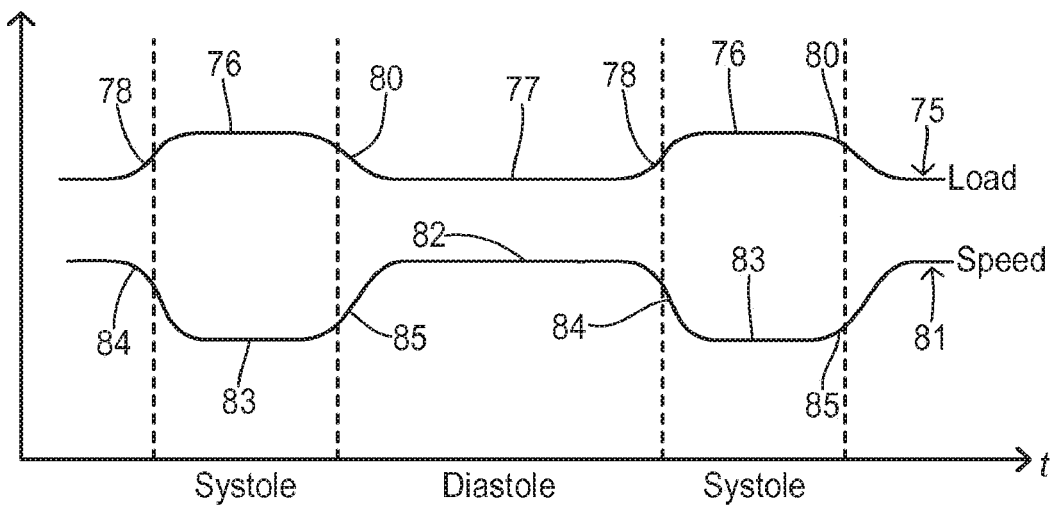
FIG. 7 is a diagram showing pump load and speed according to an embodiment using a constant current mode.

In an alternative embodiment, command calculator 70 and FOC block 66 are configured to operate the motor in a constant current mode (i.e., a constant torque mode). In this mode, the speed changes inversely with the pump load (i.e., the flow rate). Thus, an average speed is determined by the physiological monitor. The motor controller adjusts the current to obtain the desired average speed and to keep the current substantially constant. By keeping a constant current in the face of a load which varies within the cardiac cycle, the impeller speed automatically changes. FIG. 7 shows a load curve 75, wherein the load (i.e., flow rate) is high at 76 during systole and low at 77 during diastole. The load ramps up at 78 before the beginning of systole due to an increase of pressure within the ventricle and a decrease of pressure at the pump outlet (e.g., at the aorta). The load ramps down at 80 during the beginning of diastole.

In the current control mode, the pump flow increases (load increases) in the beginning of systole (at 78) and the speed curve 81 drops to a reduced speed 83. At the end of systole, the flow drops (at 80) and speed increases to an elevated speed 82. Thus, the speed increases and stays relatively high during diastole to help unload the ventricle by pumping out blood at the time it fills the ventricle. This is a natural behavior of the pump in the current control mode.

Either the variable speed control mode using a variable target speed or using the constant current approach of the invention can be combined with the conventional constant speed mode in order to adapt pump performance to the strength level of the patient's ventricle. In particular, the selection between the variable speed mode and the constant speed mode can be determined according to a physiologic capability of the patient. For example, the pump is set to operate in the constant current mode immediately following the implantation when the left ventricle is weak, thereby providing a greater level of ventricle unloading. With the patient's recovery, the pump may be set to operate in the constant speed mode, promoting higher flow pulsatility and a more natural physiologic response to the patient's activities.

What is claimed is:

1. A blood pump, comprising:
   a chamber;
   an impeller disposed within the chamber;
   a motor that is configured to drive the impeller; and
   at least one processor that:
      determines a timing of a cardio cycle of a user; and
      varies a speed of the motor based on the timing of the cardio cycle of the user such that a speed of the motor begins ramping down during a systolic phase of the cardio cycle.

2. The blood pump of claim 1, wherein:
   varying the speed of the motor comprises reducing a current level applied to the motor.

3. The blood pump of claim 1, wherein:
   an average speed of the motor is determined based on a physiological state of the user.

4. The blood pump of claim 1, wherein:
   determining the timing of the cardio cycle comprises measuring a time between current peaks.

5. The blood pump of claim 4, wherein:
   the speed of the motor begins ramping down starts at a time after one of the current peaks and before a current minimum value is detected.

6. The blood pump of claim 1, wherein:
determining the timing of the cardio cycle is based on a signal from a pacemaker.

7. The blood pump of claim 1, wherein:
the processor varies the speed of the motor based on the timing of the cardio cycle of the user such that a speed of the motor begins ramping up during a diastolic phase of the cardio cycle.

8. A blood pump, comprising:
a chamber;
an impeller disposed within the chamber;
a motor that is configured to drive the impeller; and
at least one processor that:
  determines a time period of one or both of a diastolic phase or a time period of a systolic phase of a cardio cycle of a user; and
  ramps down a speed of the motor during the systolic phase.

9. The blood pump of claim 8, wherein:
the speed of the motor is ramped down beginning at a time between about 50% and 90% into the systolic phase.

10. The blood pump of claim 8, wherein:
the speed of the motor is ramped down to a speed that is based on a physiological state of the user.

11. The blood pump of claim 8, wherein:
the speed of the motor is ramped down to a substantially constant reduced speed.

12. The blood pump of claim 8, wherein:
the speed of the motor is ramped down by reducing a current level applied to the motor.

13. The blood pump of claim 8, wherein:
the time period of one or both of the diastolic phase or the time period of the systolic phase is determined by measuring a time between current peaks.

14. A method for controlling a motor of a blood pump, comprising:
  determining a timing of a cardio cycle of a user; and
  varying a speed of the motor of the blood pump based on the timing of the cardio cycle of the user such that a speed of the motor begins ramping down during a systolic phase of the cardio cycle.

15. The method for controlling a motor of a blood pump of claim 14, further comprising:
  ramping up a speed of the motor during a diastolic phase of the cardio cycle.

16. The method for controlling a motor of a blood pump of claim 15, further comprising:
  maintaining the speed of the motor for a period of time during the diastolic phase prior to ramping up the speed of the motor.

17. The method for controlling a motor of a blood pump of claim 15, wherein:
  ramping up the speed of the motor begins at a moment between about 50% and 90% into the diastolic phase.

18. The method for controlling a motor of a blood pump of claim 15, wherein:
  the speed of the motor completes ramping up during the systolic phase of the cardio cycle.

19. The method for controlling a motor of a blood pump of claim 14, wherein:
  the speed of the motor completes ramping down during a diastolic phase of the cardio cycle.

20. The method for controlling a motor of a blood pump of claim 14, wherein:
  determining the timing of the cardio cycle is based on a signal from a current sensor of the motor.

* * * * *